United States Patent
Schönfelder et al.

(10) Patent No.: US 10,156,612 B2
(45) Date of Patent: Dec. 18, 2018

(54) METHOD FOR DETECTING SHORT-CIRCUITS IN A COIL

(71) Applicant: Siemens Aktiengesellschaft, Munich (DE)

(72) Inventors: Oliver Schönfelder, Wetter (DE); Dagmar Thien, Essen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 15/541,833

(22) PCT Filed: Dec. 3, 2015

(86) PCT No.: PCT/EP2015/078443
§ 371 (c)(1),
(2) Date: Jul. 6, 2017

(87) PCT Pub. No.: WO2016/113035
PCT Pub. Date: Jul. 21, 2016

(65) Prior Publication Data
US 2018/0017624 A1 Jan. 18, 2018

(30) Foreign Application Priority Data
Jan. 14, 2015 (EP) ..................................... 15151158

(51) Int. Cl.
*G01R 31/06* (2006.01)
*G01R 31/34* (2006.01)
(Continued)

(52) U.S. Cl.
CPC ......... *G01R 31/346* (2013.01); *G01R 19/175* (2013.01); *G01R 31/00* (2013.01);
(Continued)

(58) Field of Classification Search
CPC .... G01R 31/06; G01R 31/346; G01R 31/002; G01R 31/00; G01N 27/42; G01N 31/02
(Continued)

(56) References Cited

U.S. PATENT DOCUMENTS

| | | | |
|---|---|---|---|
| 2004/0090228 A1 | 5/2004 | Goodrich et al. | |
| 2008/0246426 A1* | 10/2008 | Aoki ................. | H02M 7/53873 318/461 |

(Continued)

FOREIGN PATENT DOCUMENTS

| | | |
|---|---|---|
| EP | 0608442 A1 | 8/1994 |
| GB | 2457590 A | 8/2009 |

(Continued)

OTHER PUBLICATIONS

EP Search Report dated Jun. 25, 2015, for EP patent application No. 15151158.1.
(Continued)

*Primary Examiner* — Jermele M Hollington
*Assistant Examiner* — Raul Rios Russo
(74) *Attorney, Agent, or Firm* — Beusse Wolter Sanks & Maire

(57) ABSTRACT

Method for detecting short-circuits in a coil in an electric machine, includes: a) arranging a coil in an air gap between the rotor and stator; c) recording signal curves generated by the coil; d) determining zero crossings of the curve and storing the times thereof; e) determining zero crossings of the curve corrected by an offset c, identifying a pair of immediately consecutive zero crossings, the time separation of which is longer than the minimum duration; f) in no pair is identified, repeating step e) until identified, wherein the offset c is varied from the zero point to a global extreme value of the curve; g) identifying at least one of the two stored times, which lies between and closest in time to the (Continued)

pair and; h) extracting two half-waves from the curve using times identified in step g), wherein each half-wave corresponds to half a revolution of the rotor.

9 Claims, 4 Drawing Sheets

(51) Int. Cl.
    *G01R 31/00*     (2006.01)
    *H02P 29/024*     (2016.01)
    *G01R 19/175*     (2006.01)
    *G01N 27/42*     (2006.01)
    *G01N 31/02*     (2006.01)

(52) U.S. Cl.
    CPC ........... *G01R 31/002* (2013.01); *G01R 31/06* (2013.01); *H02P 29/024* (2013.01); *H02P 29/0241* (2016.02); *G01N 27/42* (2013.01); *G01N 31/02* (2013.01)

(58) Field of Classification Search
    USPC ......... 324/71, 378, 403, 415, 425, 500, 537, 324/545, 765.01
    See application file for complete search history.

(56) References Cited

U.S. PATENT DOCUMENTS

| | | | |
|---|---|---|---|
| 2008/0252242 A1* | 10/2008 | Akama | H02P 6/06 318/400.14 |
| 2009/0219030 A1 | 9/2009 | Salem et al. | |
| 2011/0080127 A1* | 4/2011 | Akama | H02P 6/06 318/400.21 |
| 2012/0259563 A1 | 10/2012 | Beatty | |

FOREIGN PATENT DOCUMENTS

| | | |
|---|---|---|
| JP | S60167654 A | 8/1985 |
| JP | 2004159496 A | 6/2004 |
| JP | 2009213346 A | 9/2009 |
| WO | 2013136098 A1 | 9/2013 |

OTHER PUBLICATIONS

International Search Report dated Mar. 3, 2016, for PCT/EP2015/078443.
Albright D R, "Interturn Short-Cicuit Detector for Turbine-Generator Rotor Widings"; IEEE Transactions on Power Apparatus and Systems; vol. PAS-90, No. 2; XP011160451, pp. 478-483, ISSN 0018-9510, Mar./Apr. 1971, Schenectady NY.

* cited by examiner

METHOD FOR DETECTING SHORT-CIRCUITS IN A COIL

CROSS REFERENCE TO RELATED APPLICATIONS

This application is the US National Stage of International Application No. PCT/EP2015/078443 filed Dec. 3, 2015, and claims the benefit thereof. The International Application claims the benefit of European Application No. EP15151158 filed Jan. 14, 2015. All of the applications are incorporated by reference herein in their entirety.

FIELD OF INVENTION

The invention relates to a method for detecting rotor winding short-circuits in an electric machine.

BACKGROUND OF INVENTION

Electric machines, such as generators or motors, comprise a stator and a rotor. To generate a magnetic field, the rotor comprises a coil of electrical conductors. An insulation surrounds the electrical conductors in order to insulate them electrically against windings of the coil arranged adjacently to them and against the environment.

Faults in the insulation of the rotor can lead to winding short-circuits, that is to short-circuits between windings of the coil arranged adjacently. The result of this is that a lower exciting current flows through the short-circuited windings of the coil than through those windings of the coil that are not-short-circuited, whereby the short-circuited windings have a lower temperature than the windings that are not short-circuited. This can lead to a non-homogeneous operating temperature of the rotor. The non-homogeneous operating temperature can lead to mechanical tensions within the rotor, and the tensions can lead to a deviation of the mass distribution from the rotational symmetry. The non-symmetrical mass distribution can lead to vibrations of the rotor during operation of the electric machine. In addition, the winding short-circuit leads to a weakening of the magnetic field, which must be compensated for by a higher exciting current. The higher exciting current disadvantageously leads to a reduction in the efficiency of the electric machine.

In operation of the electric machine, winding short-circuits are determined by means of an air-gap coil measuring method, in which the magnetic flux at locations between the rotor and the stator is measured by means of a coil. For this purpose it is necessary to identify a half-rotation of the rotor in the signal curve generated by means of the coil. Since the signal curve can be overlaid by a noise signal, the identification of the half-rotation of the rotor is, however, subject to error, so that the evaluation of the air-gap coil measuring method can lead to ambiguous results.

SUMMARY OF INVENTION

The object of the invention is to provide a method for detecting winding short-circuits in a coil of an electric machine in which the recording and evaluation of the signal curve is simple, and the winding short-circuits are detectable with a high precision.

The method according to the invention for detecting winding short-circuits in an electric machine comprises the steps of: a) arranging a coil in an air gap arranged between the rotor and the stator of the electric machine; b) calculating a minimum duration of two immediately sequential zero crossings of a signal curve $U(t)$ generated by means of the coil, taking the rotational frequency and the number of pole pairs of the electric machine into account; c) recording the signal curve $U(t)$ generated by means of the coil during operation of the electric machine, having at least the duration of one revolution of the rotor; d) determining the zero crossings of the signal curve $U(t)$ and storing the times of said zero crossings; e) determining the zero crossings of the signal curve $U(t)-c$ corrected by an offset $c$, and identifying at least one pair of immediately sequential zero crossings, the time interval of which is longer than the minimum duration, where $c$ is not equal to zero; f) in the event that a pair is not identified in step e), repeating step e) until a pair is identified, wherein the offset $c$ is varied in the direction from the zero point to a global extreme value of the signal curve $U(t)$; g) identifying at least one of the two stored times which lie between and closest in time to the pair and; h) extracting two half-waves from the signal curve $U(t)$ using the times identified in step g), wherein each half-wave corresponds to half a revolution of the rotor; i) comparing the two half-waves.

Asymmetries in the magnetic field can be detected in step i) through the comparison of the two half-waves. This can, for example, be done in that the two half-waves are brought into temporal alignment, and the two half-waves are then added together. If the time-curve of the addition of the two half-waves deviates from a value of zero, then it is possible to conclude the asymmetry. On the basis of the asymmetry, it is then possible to conclude the presence of a winding short-circuit.

Not all of the zero crossings in the signal curve $U(t)$ delimit a half-wave. The times of those of the zero crossings in the signal curve $U(t)$ that truly delimit one of the half-waves are identified by the method. The method of the invention is based on the recognition that the time interval between two immediately sequential zero crossings becomes greater, the greater the offset $c$, with which the signal curve $U(t)$ is corrected, is chosen to be. The term "immediately sequential zero crossings" signifies that there is no other zero crossing between the two zero crossings. The offset $c$ is varied in increments from a minimum value up to a maximum value that is smaller than the extreme value of the signal curve $U(t)$, until the pair of immediately sequential zero crossings is found in the corrected signal curve $U(t)-c$, wherein the pair has a greater separation than the calculated minimum duration. Those of the zero crossings that truly delimit a half-wave are located temporally within the pair, and are those of the zero crossings located within the pair that are positioned temporally closest to the pair. There are two zero crossings here for each pair that truly delimit a half-wave, and in step g) it is possible to identify one or both of these zero crossings.

Because in step e) those zero crossings whose time interval is longer than the minimum duration calculated in step b) are being sought, and not those zero crossings that exactly correspond to the calculated minimum duration, the method functions advantageously and with certainty even when the actual rotation frequency deviates slightly from the rotation frequency assumed for the calculation in step b). The method also functions advantageously without using the information from a tachometer accurately measuring the speed of rotation of the rotor; rather it is sufficient to estimate approximately the minimum duration in step b).

The method can advantageously be carried out in a manner sufficiently simple that it can also be carried out automatically. Furthermore, those zero crossings that truly delimit a half-wave can be identified without error, whereby the method can be carried out with a high precision.

The method advantageously comprises the steps of: e1) determining the zero crossings of the signal curve U(t)-d corrected with an offset d, and identifying at least one pair of immediately sequential zero crossings, whose time interval is longer than the minimum duration, where d is not equal to 0 and has the opposite arithmetic sign to c; f1) in the event that a pair is not identified in step e1), repeating step e1) until a pair is identified, wherein the offset d is varied in the direction from the zero point to the other global extreme value of the signal curve U(t); and wherein in step h one of the two half-waves is extracted making use of the time points identified in step e1). If a positive offset is used to correct the signal curve U(t), upper half-waves can be identified, and if a negative offset is used to correct the signal curve U(t), then lower half-waves can be identified. In that both the positive and the negative offsets are used, both the upper and the lower half-waves can advantageously be identified. It is also possible, through a comparison of the integral of the upper half-wave with the integral of the lower half-wave, to establish whether the signal curve U(t) as a whole has an offset.

The number of pole pairs of the electric machine is advantageously one, and each of the two half-waves is delimited respectively by two of the immediately sequential times identified in step g) and/or g1). Alternatively, the number of pole pairs of the electric machine is larger than one, and each of the half-waves is formed of a number of partial waves identical to the number of pole pairs of the electric machine, wherein each partial wave is delimited in each case by two of the immediately sequential times identified in step g) and/or g1). The method can thus advantageously be carried out on an electric machine with any number of pole pairs.

It is advantageous that in steps d), e) and/or e1), the zero crossings (6 to 9) are determined by formation of $y_0=U_{t=\alpha}*U_{t=\alpha+1}$ for all the points of the signal curve U(t) and of the corrected signal curve U(t)-c, where $U_{t=\alpha}$ is a signal value in U(t) or U(t)-c, and $U_{t=\alpha+1}$ is the immediately sequential signal value. If $y_0=0$, then at least one of the two signal values is a zero crossing. If $y_0>0$, then no zero crossing is present. If $y_0<0$, then a zero crossing is present between the two signal values. Advantageously, in the case where $y_0$ is negative, the two points associated with $U_{t=\alpha}$ and $U_{t=\alpha+1}$ are linearly interpolated for determination of the zero crossing. This advantageously allows the zero crossings to be determined with a greater resolution than the time interval of the measuring points in the signal curve U(t). The linear interpolation can, for example, be carried out using the following equation:

$$0 = \frac{U_{t=\alpha+1} - U_{t=\alpha}}{t_{\alpha+1} - t_{\alpha}} \cdot (t - t_{\alpha}) + U_{t=\alpha},$$

where $t_\alpha$ is the point in time belonging to $U_{t=\alpha}$, and $t_{\alpha+1}$ is the point in time belonging to $U_{t=\alpha+1}$. The zero crossing can be determined by rearranging the equation for t.

It is advantageous for the signal curve U(t) to exhibit the electrical voltage generated in the coil or the current magnitude generated in the coil. The signal curve U(t) recorded in step c) is advantageously smoothed by means of a filter, in particular a Bezier filter, a median filter and/or a gradient filter. This allows distortions in the signal resulting from mechanical and electromagnetic influences to be overcome, so that the zero crossings can be determined with a high precision. The electric machine is advantageously a generator, in particular a synchronous machine, and/or an electric motor.

BRIEF DESCRIPTION OF THE DRAWINGS

The invention is explained in more detail below with reference to the schematic drawing attached. Here.

DETAILED DESCRIPTION OF INVENTION

Figure 10:
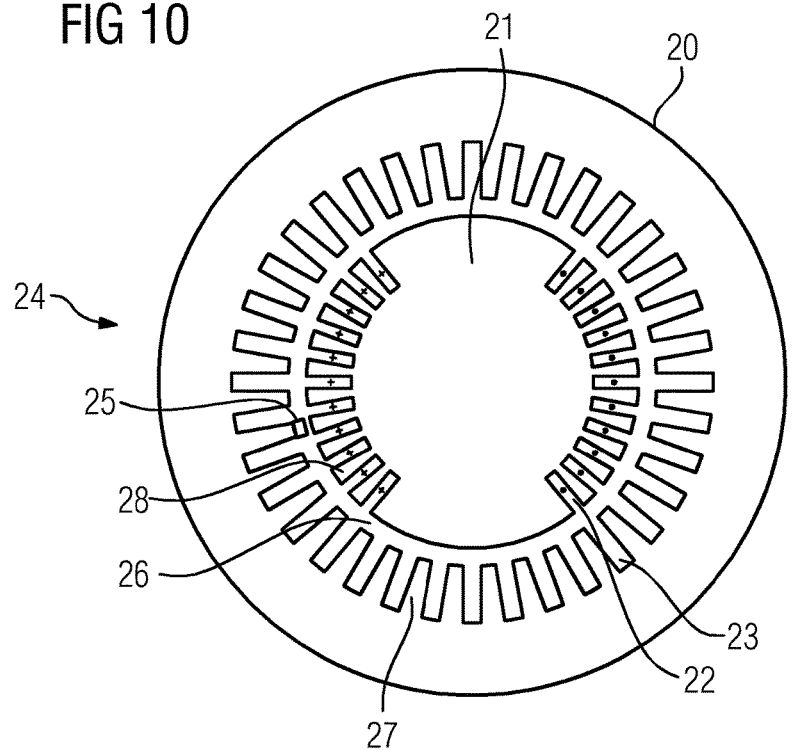
FIG. 10 shows a cross-section through an electric machine.

FIG. 10 shows a cross-section through an electric machine 24. The electric machine 24 comprises a stator 20 located radially outside, and a rotor 21 located radially inside. The stator 20 comprises a plurality of stator grooves 23 arranged adjacently to one another in the circumferential direction, into which electrical conductors are inserted. Each of the stator grooves 23 is delimited in the circumferential direction by two stator teeth 27 respectively. The rotor 21 comprises a plurality of rotor grooves 22 arranged adjacently to one another in the circumferential direction, into which electrical conductors are inserted to generate a magnetic field. A plurality of electrical partial conductors are inserted into each rotor groove 22, each of which is surrounded by an electrical insulation in order to insulate the partial conductors electrically from one another. Damage to the insulation can lead to a winding short-circuit. Each of the rotor grooves 22 is delimited in the circumferential direction by two rotor teeth 28 respectively. The number of pole pairs of the electric machine 24 in FIG. 10 is one. An air gap 26 is arranged between the stator 20 and the rotor 21. A coil 25 is inserted into the air gap 26 in order to measure a change of the magnetic flux. The coil 25 is attached in FIG. 10 to the surface of a stator tooth 27 located radially inward.

Figure 1:
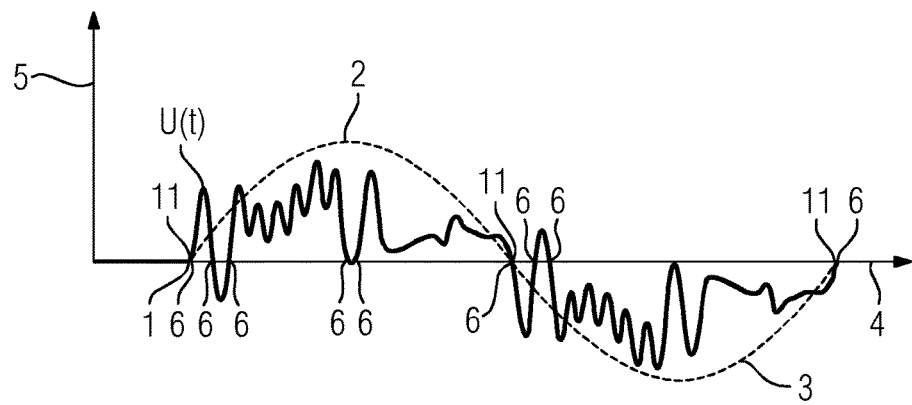
FIG. 1 shows a signal curve with a fundamental harmonic.

FIG. 1 shows a plot of a signal curve U(t) recorded by means of the coil 25. Time is plotted on the abscissa 4, and the electric voltage, or the current magnitude, is plotted on the ordinate 5. A fundamental harmonic 1 with the form $U_G=\hat{U}*\sin(\omega t)$ is also plotted, where ω is the angular frequency of the rotation of the rotor 21, and $\hat{U}$ is the amplitude. Since the number of pole pairs of the electric machine 24 is one, each oscillation period of the fundamental harmonic 1 consists of a first half-wave 2 that is characterized by a positive arithmetic sign for $U_G(t)$, and of a second half-wave 3 that is characterized by a negative arithmetic sign for $U_G(t)$. Each of the two half-waves 2, 3 corresponds to half a rotation of the rotor 21. In the method according to the invention, those sections of the signal curve U(t) that belong to the first partial wave 2 or to the second partial wave 3 are identified. A comparison of the two sections is then made. As can be seen from FIG. 1, not all the zero crossings 6 of the signal curve U(t) correspond to a zero crossing 11 of the fundamental harmonic 1. A zero crossing refers to a point in the signal curve U(t) at which U(t)=0.

Figure 2:
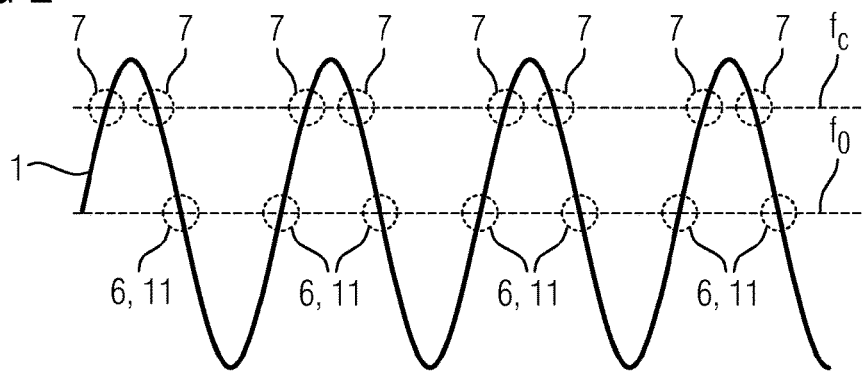
FIG. 2 shows the fundamental harmonic $U_G(t)$ with a function $f_c(t)=c$, where c>0.

The fundamental harmonic 1 is illustrated with its zero crossings 11 in FIG. 2. The zero crossings 11 are illustrated in FIG. 2 as the intersections of the fundamental harmonic 1 with the function $f_0=0$. If the signal curve $U_G(t)$ is corrected by an offset c such that the corrected signal curve adopts the form $U_G(t)$-c, the time interval between two immediately sequential zero crossings 7 changes in comparison with the zero crossings 11 of the signal curve $U_G(t)$. The zero crossings 7 of the corrected signal curve U(t)-c are illustrated in FIG. 2 as intersection points with the function $f_c(t)=c$, where c>0. The time interval here between two immediately sequential zero crossings 7 is alternately shorter and longer than the time interval between two immediately sequential zero crossings 11 of the signal curve $U_G(t)$.

Figure 3:
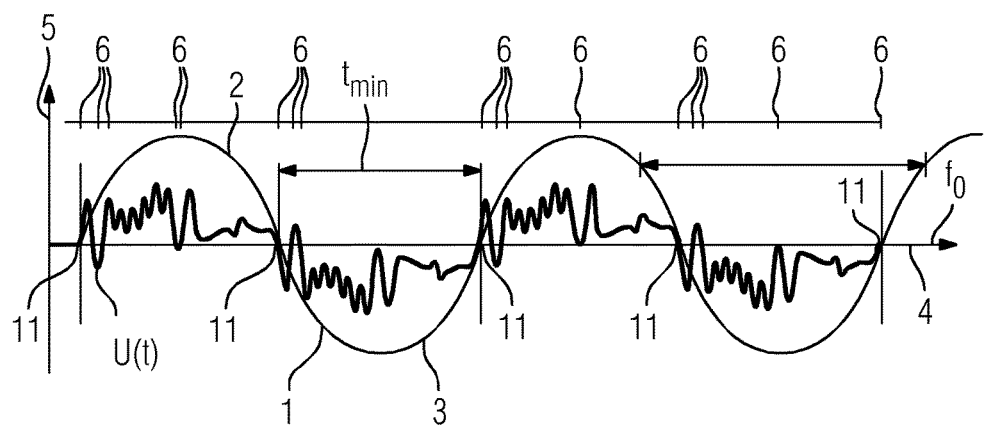
FIG. 3 shows the signal curve U(t) with one of the fundamental harmonics $U_G(t)$.

How those of the zero points 6 of the signal curve U(t) that correspond to a zero point 11 of the fundamental harmonic 1 are found is illustrated in FIGS. 3 to 6. All the zero points 6 of the signal curve U(t) are determined for this purpose, as illustrated in FIG. 3. The fundamental harmonic 1 is also shown in FIG. 3, as is a minimum duration $t_{min}$, which is the time interval between two immediately sequential zero crossings 11 of the fundamental harmonic 1. The minimum duration $t_{min}$ is estimated by the equation for the minimum duration $t_{min}=1/(f*2*n)$, where f is the frequency of rotation of the rotor 21 and n is the number of pole pairs of the electric machine 24.

Figure 4:
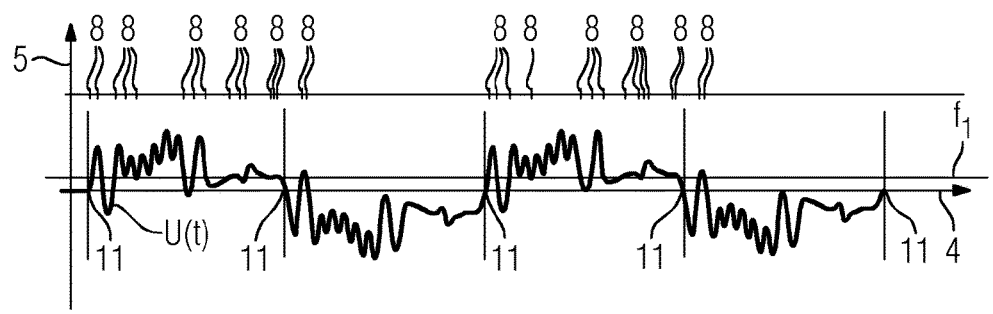
FIG. 4 shows the signal curve with a function $f_1(t)=c_1$, where $c_1>0$.

As can be seen from FIG. 4, following the determination of the zero crossings 6 of the signal curve U(t), zero crossings 8 are determined in a signal curve U(t)-$c_1$ that has been corrected by an offset $c_1$. The zero crossings 8 in the signal curve U(t)-$c_1$ are illustrated in FIG. 4 as the intersections of the signal curve U(t) with the function $f_1(t)=c_1$. To determine the offset $c_1$, the global maximum in the signal curve U(t) is first determined, and $c_1$ is then chosen to be positive and to be a fraction of the global maximum, for example to be one tenth of the global maximum. Those immediately sequential zero crossings 8 in the signal curve U(t)-$c_1$ whose time interval is greater than the minimum duration $t_{min}$ are now searched for. As can be seen in FIG. 4, such a pair of immediately sequential zero crossings 8 cannot be found in the signal curve U(t)-$c_1$ with the offset $c_1$.

Figure 5:
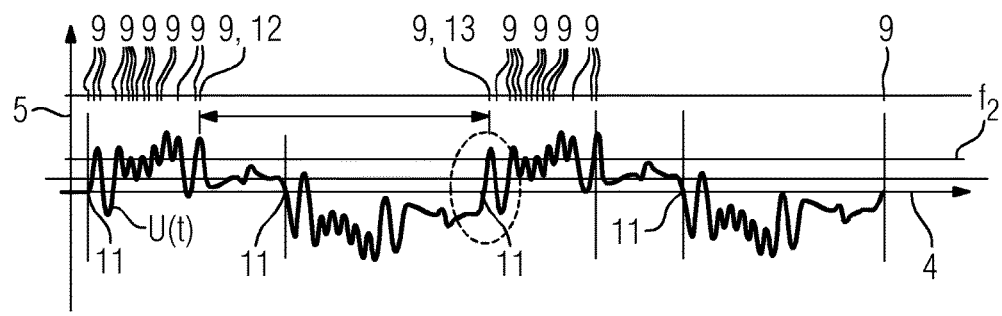
FIG. 5 shows the signal curve with a function $f_2(t)=c_2$, where $c_2>c_1>0$.
Figure 6:
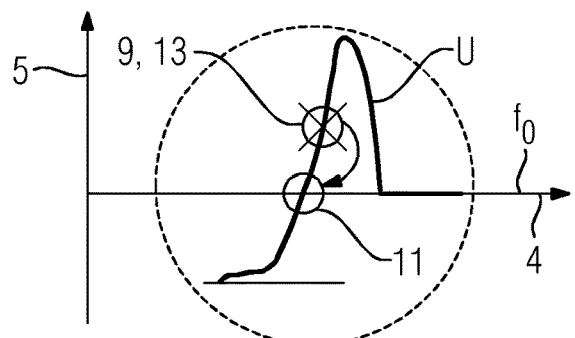
FIG. 6 shows a detail from FIG. 5, FIGS. 7, 8 show a schematic illustration of a comparison between two half-waves.

For this reason, zero crossings 9 are then determined in a corrected signal curve U(t)-$c_2$ with an offset $c_2$. The zero crossings 9 in the signal curve U(t)-$c_2$ are illustrated in FIG. 5 as the intersections of the signal curve U(t) with the function $f_2(t)=c_2$. The offset $c_2$ is here increased over $c_1$ by the fraction. Those immediately sequential zero crossings 9 in the signal curve U(t)-$c_2$ whose time interval is greater than the minimum duration $t_{min}$ are now searched for. As can be seen in FIG. 5, two such pairs of immediately sequential zero crossings 9 can be found in the signal curve U(t)-$c_2$. Each of the two pairs comprises a first zero crossing 12 and a second zero crossing 13, wherein the first zero crossing 12 is located earlier in time than the second zero crossing 13. Each of the zero crossings 6 of the signal curve U(t) that correspond to the zero crossings 11 of the fundamental harmonic 1 are identified as the zero crossings that are located in time between the first zero crossing 12 and the second zero crossing 13, and are closest in time to the first zero crossing 12 and to the second zero crossing 13. FIG. 5 shows a detail of FIG. 4, namely the second zero crossing 13, together with the zero crossing 11 of the fundamental harmonic 1.

Figure 7:
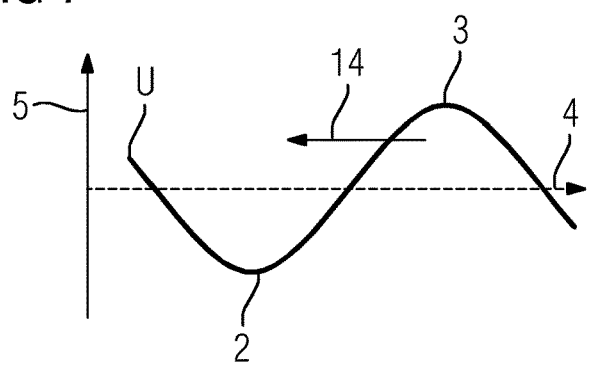
Figure 8:
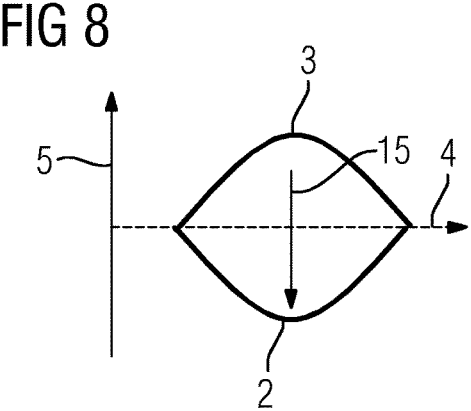

FIGS. 7 and 8 show schematically how the first half-wave 2 is compared with the second half wave 3. The respective start points and end points for the first half-wave 2 and the second half-wave 3 are extracted for this purpose from the signal curve U(t) with reference to the zero crossings 11. This can, for example, be done in that, with reference to a pair of immediately sequential zero crossings 11 of the fundamental harmonic 1 that have been found, one of the two half-waves 2, 3 is first extracted as the section of the signal curve U(t) that is delimited by the pair. The second of the two half-waves 2, 3 can, for example, be extracted as the section of the signal curve U(t) that is located earlier than the first zero crossing 12 of the pair, or after the second zero crossing 13 of the pair, by a duration that corresponds to the time interval of the pair. It is also conceivable that further zero crossings 11 of the fundamental harmonic 1 are found, in that a negative offset d is varied in the direction towards the global minimum of the signal curve U(t). Altogether three immediately sequential zero crossings 11 of the fundamental harmonic 1 can be found by varying the positive offset c and the negative offset d, wherein the two of the three zero crossings 11 that are earliest in time delimit the first half-wave 2, and the second and third in time of the three zero crossings delimit the second half-wave 3.

As can be seen from FIGS. 7 and 8, the two half-waves 2, 3 are brought into alignment by shifting one of the two half-waves 2, 3 in the direction of the abscissa 4, as is suggested by the arrow 14. The two half-waves 2, 3 are added together, as is suggested by the arrow 15 in FIG. 8. In the absence of a fault, the signal curve over time of the half-waves 2, 3 that have been added together is zero. If the signal curve of the half-waves 2, 3 that have been added together is not equal to zero, then this signal curve must be analyzed as to whether a winding short-circuit is truly present, or whether external influences have caused a corruption of the signal curve U(t).

Figure 9:
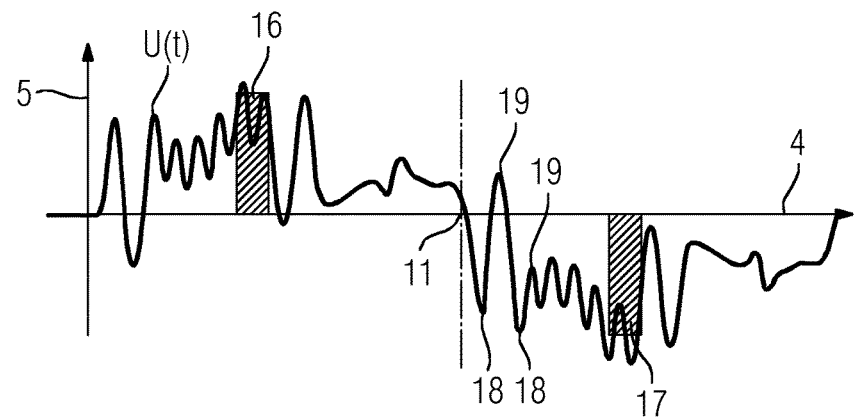
FIG. 9 shows a signal curve with two fault positions.

A typical fault case is illustrated in FIG. 9. A first fault signal 16 is present in the first half-wave 2, and a second fault signal 17 is present in the second half-wave 3. The time interval between the fault signals 16, 17 and the zero point 11 that separates the two half-waves 2, 3 from each other is identical. The fault signals 16, 17 can be associated with one of the rotor grooves 23, since a local minimum 18 in the signal curve U(t) corresponds to a rotor tooth 28, and a local maximum 19 in the signal curve U(t) corresponds to a rotor groove 23.

Although the invention has been more closely illustrated and described in more detail through the preferred exemplary embodiment, the invention is not restricted by the disclosed examples, and other variations can be derived from this by the expert without leaving the scope of protection of the invention.

The invention claimed is:

1. A method for detecting winding short-circuits in an electric machine comprising:
    a) arranging a coil in an air gap arranged between the rotor and the stator of the electric machine;
    b) calculating a minimum duration ($t_{min}$) of two immediately sequential zero crossings of a signal curve U(t) generated by means of the coil, taking the rotational frequency and the number of pole pairs of the electric machine into account;
    c) recording the signal curve U(t) generated by means of the coil during operation of the electric machine, having at least the duration of one revolution of the rotor;
    d) determining the zero crossings of the signal curve U(t) and storing the times of said zero crossings;

e) determining the zero crossings of the signal curve U(t)-c corrected by an offset c, and identifying at least one pair of immediately sequential zero crossings, the time interval of which is longer than the minimum duration ($t_{min}$), where c is not equal to zero;
f) in the event that a pair is not identified in step e), repeating step e) until a pair is identified, wherein the offset c is varied in the direction from the zero point to a global extreme value of the signal curve U(t);
g) identifying at least one of the two stored times which lie between and closest in time to the pair, and;
h) extracting two half-waves from the signal curve U(t) using the times identified in step g), wherein each half-wave corresponds to half a revolution of the rotor;
i) comparing the two half-waves.

2. The method as claimed in claim 1, further comprising:
e1) determining the zero crossings of the signal curve U(t)-d corrected with an offset d, and identifying at least one pair of immediately sequential zero crossings, whose time interval is longer than the minimum duration ($t_{min}$), where d is not equal to 0 and has the opposite arithmetic sign to c;
f1) in the event that a pair is not identified in step e1), repeating step e1) until a pair is identified, wherein the offset d is varied in the direction from the zero point to the other global extreme value of the signal curve U(t); and wherein in step h one of the two half-waves is extracted making use of the time points identified in step e1).

3. The method as claimed in claim 1,
wherein the number of pole pairs of the electric machine is one, and
each of the two half-waves is delimited respectively by two of the time points identified in step g) and/or
g1) that are immediately sequential.

4. The method as claimed in claim 3,
wherein the number of pole pairs of the electric machine is larger than one, and each of the half-waves is formed of a number of partial waves corresponding to the number of pole pairs,
wherein each partial wave is delimited in each case by two of the immediately sequential times identified in step g) and/or g1).

5. The method as claimed in claim 2,
wherein in steps d), e) and/or e1), the zero crossings are determined by formation of $y_0 = Ut=\alpha * Ut=\alpha+1$ for all the points of the signal curve U(t) and of the corrected signal curve U(t)-c, where $Ut=\alpha$ is a signal value in U(t) or U(t)-c, and $Ut=\alpha+1$ is the immediately sequential signal value.

6. The method as claimed in claim 5,
wherein, in the case where $y_0$ is negative, the two points associated with $Ut=\alpha$ and $Ut=\alpha+1$ are linearly interpolated for determination of the zero crossing.

7. The method as claimed in claim 1,
wherein the signal curve U(t) exhibits the electrical voltage generated in the coil or the current magnitude generated in the coil.

8. The method as claimed in claim 1,
wherein the signal curve U(t) recorded in step c) is smoothed by means of a filter, a Bezier filter, a median filter and/or a gradient filter.

9. The method as claimed in claim 1,
wherein the electric machine is a generator, a synchronous machine, and/or an electric motor.

* * * * *